United States Patent
Ulsø

(10) Patent No.: US 6,860,737 B2
(45) Date of Patent: Mar. 1, 2005

(54) INSTRUMENT FOR INTERPROXIMAL CONTACT BETWEEN A PLASTIC FILLING AND AN ADJACENT TOOTH SURFACE

(76) Inventor: Jens Ulsø, Alsvej 25, DK-8240 Risskov (DK), 8240

( * ) Notice: Subject to any disclaimer, the term of this patent is extended or adjusted under 35 U.S.C. 154(b) by 0 days.

(21) Appl. No.: 10/468,807

(22) PCT Filed: Feb. 25, 2002

(86) PCT No.: PCT/DK02/00123
§ 371 (c)(1),
(2), (4) Date: Dec. 2, 2003

(87) PCT Pub. No.: WO02/069832
PCT Pub. Date: Sep. 12, 2002

(65) Prior Publication Data
US 2004/0086829 A1 May 6, 2004

(30) Foreign Application Priority Data
Feb. 23, 2001 (DK) .................................. PA 2001 00302

(51) Int. Cl.[7] .............................................. A61C 3/00
(52) U.S. Cl. ...................................... 433/141; 433/163
(58) Field of Search .............................. 433/2, 39, 40, 433/141, 148, 149, 163

(56) References Cited

U.S. PATENT DOCUMENTS

| 804,099 A | * | 11/1905 | Chase ....................... 433/163 |
| 4,726,770 A | | 2/1988 | Kurer |
| 4,747,777 A | | 5/1988 | Ward |
| 4,836,781 A | | 6/1989 | Meinershagen |
| 5,039,302 A | * | 8/1991 | Keys ............................. 433/3 |
| 5,318,446 A | | 6/1994 | Slone |
| 6,575,749 B1 | * | 6/2003 | Greenwald .................. 433/141 |

FOREIGN PATENT DOCUMENTS

WO     WO 97/38925     10/1997

* cited by examiner

*Primary Examiner*—Cary E. O'Connor
(74) *Attorney, Agent, or Firm*—James Creighton Wray; Meera P. Narasimhan

(57) ABSTRACT

The invention relates to a tool for establishing correct interproximal contact between a tooth that has been bored out and the cavity filled with plastic filling, and an adjacent tooth with a contact surface directed towards the bored out tooth referred to, with plastic filling. The tool is provided with two outer pins and a central pin. The outer pins create stability for the tool, when a head of the tool, and from where the pins extend, is arranged in the bored out cavity. The central pin ensures, together with the outer pins and facing outs between the pins, that it is possible to establish the correct interproximal contact for the plastic filling against the contact surface of the adjacent tooth.

11 Claims, 2 Drawing Sheets

INSTRUMENT FOR INTERPROXIMAL CONTACT BETWEEN A PLASTIC FILLING AND AN ADJACENT TOOTH SURFACE

This application claims the benefit of Danish Application No. PA 2001 00302 filed Feb. 23, 2001 and PCT/DK02/00123 filed Feb. 25, 2002.

BACKGROUND OF THE INVENTION

The present invention relates to a tool for establishing interproximal contact between a plastic filling in a bored out tooth cavity and a contact surface on an adjacent tooth, the tool having a head with a first convex surface facing forward relative to a handle, the head being configured to fit into the bored out cavity in the tooth, such that the head extends from the handle on the tool and downwards into the cavity, and where the head includes pins that are separated by interstice.

U.S. Pat. No. 5,318,446 describes such a tool. The tool is made from transparent plastic. The tool has a head that includes two pins. On one side, the pins have convex surfaces and on the other side, the pins have plane surfaces. The convex surface is designed to press plastic into a plastic filling and a matrix band that is arranged around the tooth for outward contact with the contact surface on the adjacent tooth. Hereafter, the plastic is hardened by means of light from a light source through the transparent tool. After this, the tool is removed, and the holes in the plastic filling caused by the pins are refilled with plastic filling material and are hardened with the light source.

This tool does, however, have some disadvantages. The tool has two separate pins. An interstice is established between the pins. The interstice is exactly opposite the most projecting point of the adjacent tooth surface when the tool is arranged in the cavity in the tooth. The matrix band that runs between the tool and the adjacent tooth is made from a very thin metal foil. Thus, there will be the risk that the matrix band at the position of the interstice in the tool will bend inwards against the interproximal cavity in the tooth away from the adjacent tooth surface and create a distance between the matrix band and the adjacent tooth surface. This implies that the interproximal contact between the adjacent teeth is not obtained at all, and the plastic filling's contact surface is thereby lost at a substantial and critical place. Moreover, the pins on the tool take up a lot of space in the bored out interproximal cavity, which makes it difficult to see the work during the plastic filling. This also means that the holes after the pins, when the first plastic filling is performed, are very large, which implies that a large part of the plastic filling against the adjacent tooth surface is performed without the matrix band being pressed outwards at the same time. Therefore, the matrix band can also risk not having interproximal contact to the adjoining tooth during the following plastic filling and final hardening. Moreover, the contact surface of the tool is only convex in one plane, which gives an insufficient contact against the adjoining tooth. Moreover, the tool is elastic, which make the application in the working process unstable.

U.S. Pat. No. 4,726,770 describes a transparent glass wedge for placement in a filling in a cavity in a tooth. The glass wedge has a convex surface facing forward with a so-called "knuckle", and by means of a handle and plastic in the plastic filling, the knuckle presses the matrix band and the plastic outwards against the contact surface on the adjacent tooth. Hereafter, the plastic is hardened through the transparent glass wedge, and after that, the glass wedge continues to be part of the filling. The knuckle on the wedge is made in such a way that when the tip of the wedge rests at the bottom of the cavity in the tooth, then the knuckle will be directly opposite the point on the adjacent tooth where the interproximal contact must be established. Until the filling is hardened, the wedge is maintained pressed outwards against the matrix band by means of a handle. When the filling is hardened, the glass wedge remains in the filling, and thus makes up part of the filling in the cavity.

This means for filling does not make up a tool as such, but makes up an actual part of the filling, which remains inside the filling. However, the wedge is supplied with a so-called "kuckle", which is to ensure that the interproximal contact between the adjacent teeth remains at exactly one single point. However, the wedge only obtains the desired effect, if the knuckle is made exactly opposite the corresponding convexity on the side of the adjacent tooth. If the knuckle is made too high or too low in relation to this, then the desired effect will not be obtained. This means that each wedge must be shaped individually in consideration of the dental patient in question and in consideration of the individual bored out cavities' shape and size, particularly upwards and downwards. It is moreover difficult to maintain the wedge with adequately large pressure outwards against the matrix band with adequately large pressure and out against the contact surface on the adjacent tooth. Moreover, there is a disadvantage that part of the filling is made of glass, while another part of the filling is made of another material. Thus, there will be a large risk that the glass wedge slides out of the filling, if the two materials, respectively glass and for example plastic react differently under given influences such as hot and cold drinks, mechanical strain, when chewing is performed etc.

SUMMARY OF THE INVENTION

It is the object of the present invention to provide a tool that does not cause the aforementioned disadvantages to arise, which at the same time is easy for any dentist to apply, and which does not require special manufacturing, i.e. is independent of patient or his/her teeth and independent of size and shape of the bored out interproximal cavity.

This object is obtained with a tool that is characterized in that the head includes two outer pins and a central pin.

By providing the tool with three pins, which include two outer pins and a central pin, on the one hand, a sufficient securing of the tool in the cavity in the tooth in relation to the adjacent tooth surface is obtained, but it is also achieved that the interproximal contact is established such that is ensures that the matrix band makes contact with the adjacent tooth surface exactly where the contact surface is going to be established.

In a preferred embodiment, the tool is characterized in that the central pin has a length l that is between one and a quarter times the length L of the outer pins, preferably half of the length of L, and preferably further characterized in that the pins also have a convex surface facing forward relative to the handle and that the surface of the pins runs along a largely continuous, preferably double continuous, curved surface, such that the surface of the central pin is protruding relative to the surface of the outer pins.

By making the central pin shorter than the outer pins, the advantage is obtained that it is unambiguously the outer pins that position the head of the tool in relation to the matrix band and in relation to the contact surface on the adjacent tooth, and it is unambiguously the central pin that indicates the interproximal contact with the contact surface on the adjacent tooth. When the curved surface provided by the surface of the pins at the same time is shaped in such a way that the surface of the central pin is protruding in relation to the surface of the outer pins, then the security is increased further in order for the interproximal contact to be established by the central pin.

In a further preferred embodiment, the head, in relation to the handle, also has a second convex surface facing backward, and the pins also create, in relation to the handle, a convex surface facing backward, and the surface of the pins facing backward runs along a largely continuous outward curved surface, such that the surface of the central pin is protruding in relation to the surface of the outer pins.

If both a surface facing forward and a surface facing backward on the pins are convex, then it will be possible to apply the same head for filling, independent of whether the filling is performed in a cavity that faces forward in the tooth in relation to the handle's introduction in the mouth or whether the filling is performed in a cavity that faces backward in relation to the handle's introduction in the mouth.

A further preferred embodiment is characterized in that the outer pins have a sideways exterior that ends in an outer tip, and that a transition between the sideways exteriors and the outer tips are rounded. By providing that the tips of the outer pins are rounded, it is obtained that that no damage is done to the gums or other delicate parts of the cavity of the mouth, when the tool is applied. The rounded tips also prevent notch marks in the thin foil from which the matrix band is made.

BRIEF DESCRIPTION OF THE DRAWINGS

The invention will hereafter be described in more detail referring to the enclosed drawing, where.

DETAILED DESCRIPTION OF THE PREFERRED EMBODIMENTS

Figure 1:
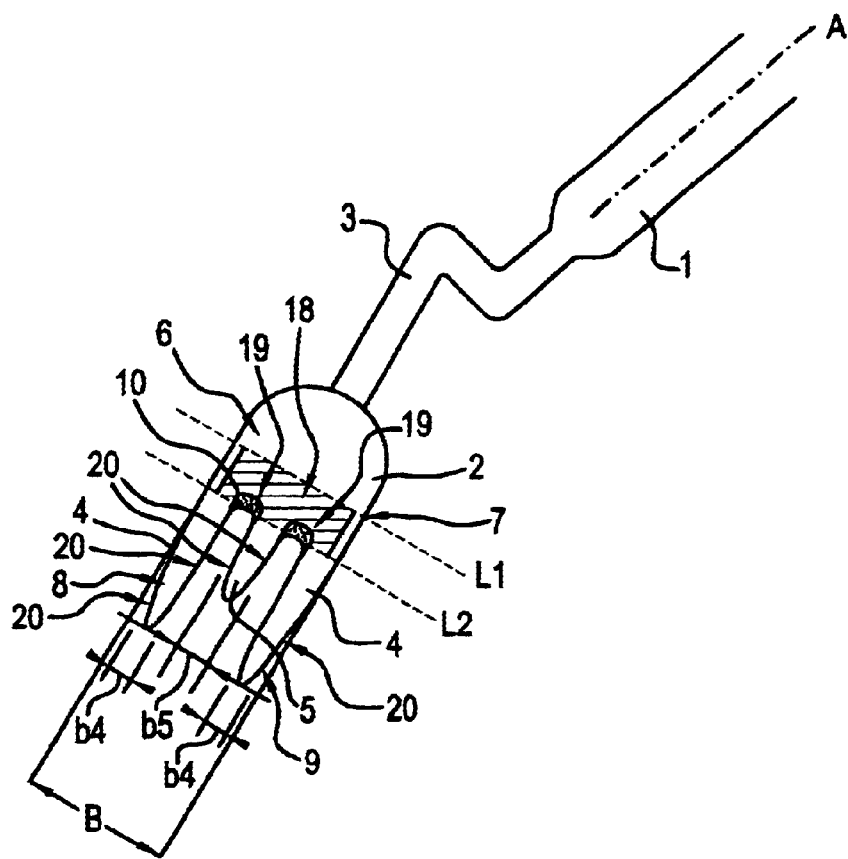
FIG. 1 is a picture in perspective of a tool according to the invention.
Figure 2:
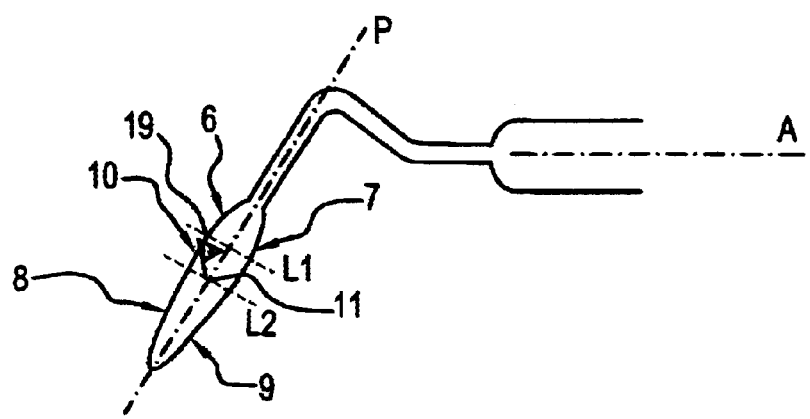
FIG. 2 is a side view of the tool according to the invention.

FIG. 1 and FIG. 2 show a possible embodiment of a tool according to the invention. The tool includes a handle 1 and a head 2 that are mutually connected with a transition piece 3. The head 2 is supplied with two outer pins 4 and a central pin 5 that extend from the head 2 and tilted downwards in relation to a longitudinal axis A for the handle 1. The outer pins have a length L, and the central pin 5 has a length l. The length l is smaller than the length L and preferably around half of the length L.

The head 2 has a front surface 6 and a rear surface 7 (see FIG. 2). Both surfaces 6,7 are convex and run along a double curved continuous surface at each side of the head 2. Each of the pins 4,5 also has a front surface 8 and a rear surface 9 that run along the same double curved continuous surface. By letting both the front surface 6,8 and the rear surface 7,9 be curved, it is possible to apply the same head 2 for fillings at each side of a tooth, i.e. where the handle and the head are either pushed forward, when the tool is applied, or the handle and the head are pulled backward, when the tool is applied.

Alternatively, it will however be possible only to let the front surface 6,8 be curved. In relation to a plane P through the head 2, the curved surfaces have an outer point 10, 1 that is on the central pin 5, preferably between the upper and the centre of the central pin, alternatively above the upper part of the central pin 5. In the most preferred embodiment, the outer point 10,11 is at a height that corresponds to the height of the upper point in the concave recesses 19, which are illustrated in FIG. 1 and FIG. 2. A contact face 18 is created in a transition between the surfaces 6 and 8, respectively between the surfaces 7 and 9. The transition is created between an upper line L1 and a lower line L2. The contact face 18 is going to be the tool's contact face with the contact surface 17 on the adjacent tooth 15 (see FIG. 3). The lines L1 and L2 are mainly imaginary but can be marked on the surfaces 6,8, respectively the surfaces 7,9, so that the dentist can see that the contact with the contact surface 17 on the adjacent tooth 15 (see FIG. 3) must be established between the lines L1 and L2. The head 2 may end just above the upper line L1, as the upper part of the head is not applied during plastic filling.

In the transition between the surfaces 6,8 respectively the surfaces 7,9, and between the pins 4,5, concave recesses are provided, which are shown as dark areas on FIG. 1 and as concave stippled curve on FIG. 2. The recesses 19 provide a rounded transition between the front 6 and the back 7 of the head 2 and contribute to that light for hardening of the plastic filling can pass easier through the plastic filling from the front 6 to the back 7 of the head 2, or the vice versa. The recesses 19 allow room for plastic, which after light hardening further keeps the matrix band outwards for good contact with the adjacent tooth surface. The contact face 18, which is created in the transition between the surfaces 6,8 respectively 7,9, and which is shown with hatching, can be slightly rough in the surface such that the head 2 does not slide as easily on the smooth matrix band (see FIG. 3) when the matrix band is pressed outwards for contact with the adjacent tooth. In practice however, it has been found that this causes scratches in the matrix band and rough surfaces in the adjacent tooth. In a further development of the invention, a smooth contact face 18 is therefore preferred.

The sides 20 of the pins 4,5 are largely plane, smooth and parallel with each other. All sides on the three pins 4,5 converge towards the tip of the pins. This contributes to that the pins 4,5 and thereby the tool can be loosened from the hardened plastic. Transitions between the sides 20 of the pins 4,5 and the front 8, respectively the back 9 of the pins 4,5 are slightly rounded, and the tip of the pins are furthermore rounded. This ensures that the pins 4,5 of the tool do not create embossings on the matrix band that can cause notches to develop when the matrix band is pressed out for contact with the adjacent tooth surface (see FIG. 4), and which, if occasion should arise, could damage the matrix band and provide a rough interproximal contact.

I the shown embodiment, the surfaces 6, 7, 8, 9 are double curved, such that the curved surfaces in relation to the plane P through the head 2 exactly have an outer point 10,11 each. Alternatively, it will be possible to let the surfaces 6, 7, 8, 9 be single curved, such that the curving can either only take place from the head 2 and downward along the pins 4,5, or only take place across the head 2 and across the pins 4,5. Then, the curved surfaces will not have points, but a line instead (not shown), which in relation to the plane P through the head constitute the outer most part of the surfaces and which either runs across or along the head 2, respectively the pins 4,5, depending on how the surface 6, 7, 8, 9 curves in relation to the plane P through the head 2.

The outer pin 5 and the central pin 4 have at the top of the pins a total width b4,b5 that is at least half, preferably ⅗ of the total transversal width B of the head 2, exactly where the pins extend from the head 2. Moreover, the central pin 4 and the outer pins 5 are rounded, so front and rear, respectively side face, create a rounded transition. This means that there is no risk that the outer pins will damage the patient when applying the tool.

Figure 3:
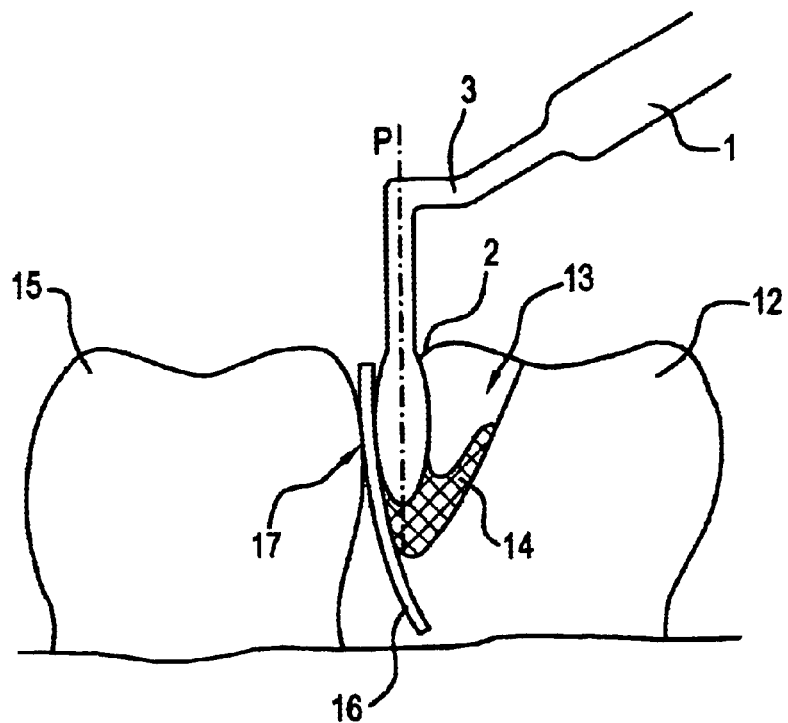
FIG. 3 shows the tool applied in a bored out tooth against an adjacent tooth.

FIG. 3, on the one hand, shows a tooth 12, wherein a cavity 13 has been bored out and is subsequently partially filled with plastic filling 14, and, on the other hand, an adjacent tooth. Between the concerned tooth 12 and the adjacent tooth 15, a so-called matrix band 16 runs. The adjacent tooth 15 has a contact face 17 facing the concerned tooth 12. Since the concerned tooth 12 has been bored out, the contact face for the concerned tooth 12 is no longer present but must be restored by plastic filling by means of the tool.

Figure 4:
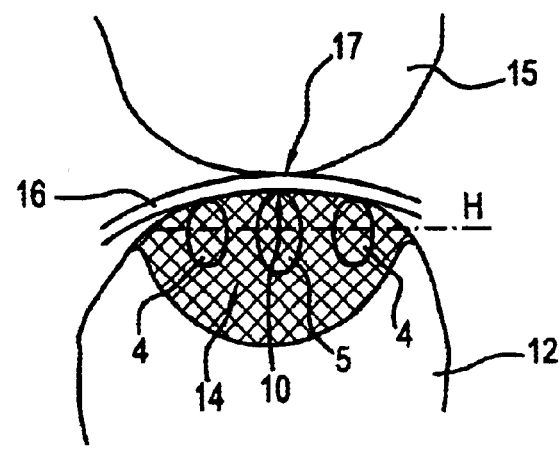
FIG. 4 shows a section in a plastic filling by the tool according to the invention after interproximal contact is established with the adjacent tooth surface.

FIG. 4 is a section in the plastic filling with the outer pins 4, respectively the central pin 5, of the tool according to the invention. The outer pins 4 have a thickness t4 that is smaller than the thickness t5 of the central pin 5. It is clear from the section shown that the central pin 5 provides the front contact surface and, thus, ensures that the matrix band abuts the adjacent tooth 15 corresponding exactly to the contact face 18 of the tool in the transition between the surfaces 6 and 8, respectively the surfaces 7 and 9. This contact surface can by means of the tool very easily be created exactly opposite the contact surface 17 on the adjacent tooth 15.

By merely tilting the plane P, and thereby the head 2 and the pins 4,5, (see FIG. 3) back or forth about a horizontal axis H (see FIG. 4), it will be possible to establish the interproximal contact between the matrix band 16 and the adjacent tooth 15, such that the filling subsequently will show a contact surface directly opposite the corresponding contact surface 17 on the adjacent tooth 15.

I a preferred embodiment, the head, alternatively the pins, are supplied with the reference lines L1 and L2 (see FIG. 1) just above and just below the outer point 10, for example approximately ½ nm above and approximately ½ mm below. Between the lines L1 and L2, the interproximal contact is established. It makes it easier to refind, where on the tool the contact surface must be established with the matrix band 16 and, thereby, with the contact surface on the adjacent tooth 15.

The tool according to the invention is mainly made from hardened stainless steel. This means that it is not immediately possible to harden plastic fillings with light, if the filling is placed behind one of the pins. However, due to the creation of recesses in the interstices between the pins, the plastic's ability to lead the light will be sufficient to harden the plastic between the pins, behind the pins, and up in the recesses between the pins. Since the plastic filling is broken in several places by applying the tool's head and due to a central pin between the outer pins, the total shrinking of the plastic during the hardening will moreover be reduced.

When the first part of the plastic filling has finished hardening, the pins are pulled out of the plastic filling and refilling is done in the cavities left by the pins, after which this refilling is finally hardened. This part of the first filling, which is created in the interstices between the pins, is sufficient to keep the matrix band outward when the pins are pulled up from the first part of the filling and, subsequently, the cavities of the pins in the filling are filled.

The invention above is described referring to a specific embodiment for a tool according to the invention. It will however, be possible to make variations, such that, for example, the central pin, in relation to the outer pins, has another length and/or another width, or that the sideways extent of the pins is larger or smaller in relation to the total sideways extent of the head The size, such as the width and/or the length of the head itself in relation to the length and the width of the pins can also be larger or smaller than the size shown. Moreover, it will be possible to make the front and the rear surface of the head and the pins more or less curved than shown.

What is claimed is:

1. Tool for establishing interproximal contact between a plastic filling in a bored out cavity in a tooth and a contact surface on an adjacent tooth, the tool having a head with a first convex surface facing forward relative to a handle, the head being configured to be lead down into the bored cavity in the tooth, such that the head extends downwards into the cavity, and where the head includes two pins that are separated by interstices, wherein the head includes two outer pins and a central pin.

2. Tool according to claim 1, wherein the outer pins have a first length L, and the central pin has a length l that is shorter than the length L.

3. Tool according to claim 1, wherein the central pin has a length l that is between one and a quarter times the length L of the outer pins, preferably half of the length of L.

4. Tool according to claim 1, wherein the pins also have a convex surface facing forward relative to the handle and the surface of the pins runs along a largely continuous, preferably double continuous, curved surface, such that the surface of the central pin relative to a plane P through the head is protruding relative to the surface of the outer pins.

5. Tool according to claim 1, wherein the pins have a total width b4, b5 across the head that is at least 0.5 times the total transverse width B of the head, preferably has an extent of 0.6 times the total transverse width B of the head.

6. Tool according to claim 1, wherein the head also has a second convex surface facing backwards relative to the handle and also the pins have a convex surface facing backwards relative to the handle, and the surface of the pins facing backward runs along a largely continuous outwardly curved surface, such that the surface of the central pin in relation to a plane P through the head is protruding relative to the surface of the outer pins.

7. Tool according to claim 1, wherein the outer pins and the central pin end in each their tip, and the tips are rounded.

8. Tool according to claim 1, wherein an upper reference line L1 and a lower reference line L2 are provided on the front surface of the head, respectively the front surface on the pins.

9. Tool according to claim 8, wherein recesses are made up between the pins and between the lines L1 and L2.

10. Tool according to claim 8, wherein an upper reference line L1 and a lower reference line L2 are provided also on the rear surface of the head, respectively the rear surface on the pins.

11. Tool according to claim 1, wherein the contact face of the tool has a smooth surface, where the contact face is the face that is in contact with the adjacent tooth's contact surface.

* * * * *